United States Patent
Kleiner

(10) Patent No.: US 9,672,640 B2
(45) Date of Patent: Jun. 6, 2017

(54) METHOD FOR INTERACTIVE MANUAL MATCHING AND REAL-TIME PROJECTION CALCULATION IN IMAGING

(71) Applicant: Varian Medical Systems International AG, Zug (CH)

(72) Inventor: David Kleiner, Zurich (CH)

(73) Assignee: Varian Medical Systems International AG, Cham (CH)

( * ) Notice: Subject to any disclaimer, the term of this patent is extended or adjusted under 35 U.S.C. 154(b) by 0 days.

(21) Appl. No.: 13/749,498

(22) Filed: Jan. 24, 2013

(65) Prior Publication Data
US 2014/0205167 A1 Jul. 24, 2014

(51) Int. Cl.
| | |
|---|---|
| G06T 11/00 | (2006.01) |
| A61B 6/03 | (2006.01) |
| A61B 6/00 | (2006.01) |
| A61N 5/10 | (2006.01) |
| A61B 5/00 | (2006.01) |

(52) U.S. Cl.
CPC .......... *G06T 11/008* (2013.01); *A61B 5/0033* (2013.01); *A61B 6/032* (2013.01); *A61B 6/5223* (2013.01); *A61B 6/5235* (2013.01); *A61N 5/1049* (2013.01); *A61N 2005/1062* (2013.01)

(58) Field of Classification Search
None
See application file for complete search history.

(56) References Cited

U.S. PATENT DOCUMENTS

| | | | | |
|---|---|---|---|---|
| 7,848,592 B2* | 12/2010 | Chen | .......................... | G06T 7/35 382/128 |
| 2002/0038118 A1* | 3/2002 | Shoham | .............. | A61B 17/1757 606/1 |
| 2007/0127845 A1* | 6/2007 | Fu | ......................... | A61B 6/4458 382/294 |
| 2009/0148023 A1* | 6/2009 | Spahn | ................... | A61B 6/4208 382/132 |
| 2011/0170756 A1* | 7/2011 | Schneider | ............... | G06T 15/08 382/131 |
| 2011/0182492 A1* | 7/2011 | Grass | .................... | A61B 6/4441 382/131 |
| 2012/0163686 A1* | 6/2012 | Liao | .......................... | G06T 7/33 382/130 |
| 2013/0108133 A1* | 5/2013 | Inoue | .................... | G06T 3/0037 382/131 |

\* cited by examiner

*Primary Examiner* — Tsung-Yin Tsai

(57) ABSTRACT

Methods and systems are proposed herein for performing manual matching of generated digitally reconstructed radiographs with acquired verification images efficiently without intensive processing and/or memory consumption or hardware requirements. According to one aspect of the claimed subject matter, a system is provided that includes a computing workstation, communicatively coupled to both a data storage device and an image acquisition device. Real time images acquired by the image acquisition device are presented to the user along with one or more digitally reconstructed radiographs (DRRs)—generated using dynamically selected rendering techniques—from previously acquired image data. The user is able to verify the DRRs as a match to the real time image, or, alternately, to dynamically generate additional DRRs more suitable by actuating a portion of the generated DRR. Based on the user actuation, a new DRR is generated and presented to the user for verification.

26 Claims, 7 Drawing Sheets

Exemplary Computer System 500

700a

700b

700c

METHOD FOR INTERACTIVE MANUAL MATCHING AND REAL-TIME PROJECTION CALCULATION IN IMAGING

Radiology is the branch of medical science dealing with medical imaging for the purpose of diagnosis and treatment. The practice of radiology often involves the usage of X-ray machines or other radiation devices to perform the diagnosis or administer the treatment. Other practices of radiology employ techniques that do not involve radiation, such as magnetic resonance imaging (MRI) and ultrasound. As a medical field, radiology can refer to two sub-fields, diagnostic radiology and therapeutic radiology.

Diagnostic radiology deals with the use of various imaging modalities to aid in the diagnosis of a disease or condition in a subject. Typically, a wide beam of X-rays at a relatively low dosage is generated from a radiation source and directed towards an imaging target. An imager positioned on the opposite side of the source with respect to the imaging target receives the incident radiation and an image is generated based on the received radiation. Newer technology and advanced techniques allow for improved image collection with the application of computerized tomography (CT) to medical imaging techniques. Conventional medical imaging processes involving CT scans typically produce a series of 2-dimensional images of a target area which can be subsequently combined using computerized algorithms to generate a 3-dimensional image or model of the target area.

Therapeutic radiology or radiation oncology involves the use of radiation to treat diseases such as cancer through the directed application of radiation to targeted areas. In radiation therapy, radiation is applied (typically as a beam) to one or more regions of the targeted area at pre-specified dosages. Since the radiation can be potentially harmful, extensive treatment planning may be conducted, sometimes far in advance of the actual treatment sessions, to pinpoint the exact location(s) to apply the beam, and to limit unnecessary exposure to the radiation to other areas in the subject. The treatment planning phase may include the performance of CT scanning or other medical imaging techniques to acquire image data, that can be subsequently used to precisely calculate the proper position and orientation of the subject, location of one or more target areas within the subject, and the required dosage(s) of the radiation applied during therapy.

Since the treatment planning stage may precede the actual therapy session by a substantial period of time, further imaging may be performed immediately prior to, and/or in conjunction with the application of radiation for therapy to verify the position and orientation of the subject and target area during therapy. The images acquired during the treatment application (and/or in the positioning period immediately prior to the treatment application) are compared to stored image data acquired during the treatment planning stage. Typically, an automatic process is performed by computer-implemented software that matches the images acquired during treatment (or positioning) with the stored image data. Unfortunately, automatic matching is not always effective or accurate. On these occasions, manual matching of the acquired verification image with a reference image (generated from stored, previously acquired planning images) is required.

Manual matching is typically performed by a radiologist, technician, or other such user through a computing system to confirm the match of characteristics in a target region of a subject as displayed in a produced verification image with the same characteristics of the same subject in a previously acquired "reference" image. Typically, one or more digitally reconstructed radiographs, or "DRRs" are generated from the pre-acquired planning images and displayed to the user alongside the verification image. A user is then able to verify or reject the generated DRR as a match with the acquired verification. A confirmed match could result in a registration between the generated DRR and the acquired verification image. If rejected, additional reference images are generated from the subject's previously acquired image data for the user's review.

Due to the demands of rendering these images quickly and clearly, generation of additional DRRs from the stored planning image can be rather processing intensive and/or memory intensive. Conventional methods for generating DRRs may include a GPU accelerated method, wherein a high performing graphics processing unit (GPU) is used to speed up the calculation of DRRs. Unfortunately, this requires that the computing system being used for manual matching actually have a high powered GPU. Machines without a discrete GPU or machines without high powered GPUs may not have sufficient capability for volume rendering.

Another solution is directed to generating DRRs using attenuation field based methods. According to these practices, an attenuation field is either pre-calculated or calculated on the fly for the desired image or scene. This attenuation field is then used as a lookup table for the actual algorithm used to generate the DRR. Yet another solution involves a shear warp method that provides quick volume rendering using a shear warp factorization of the transformation between generated DRRs. However, the creation and maintenance of an attenuation field can easily require expensive pre-computation and memory consumption. Likewise, the shear warp method, can also be extremely processing-heavy and require additional memory to perform, and as such neither is particularly ideal for generating multiple DRRs efficiently.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

Methods and systems are proposed herein for performing manual matching of generated digitally reconstructed radiographs with acquired verification images efficiently without intensive processing and/or memory consumption or hardware requirements. According to one aspect of the claimed subject matter, a system is provided that includes a computing workstation, communicatively coupled to both a data storage device and an image acquisition device. In one embodiment, a user of the workstation is able to access and load previously acquired image data for a subject from the data storage device into the local memory of the workstation. Images acquired by the image acquisition device are presented to the user as "verification" images and one or more digitally reconstructed radiographs (DRRs) generated from the previously acquired image data are displayed as "reference" images adjacent to, or otherwise immediately proximate to the verification images. In still further embodiments, the generated DRR may be super-imposed (overlaid) directly over the verification images. The user is able to verify the DRRs as a match to the verification image by visually matching characteristic regions, or, alternately, to dynamically generate additional DRRs that may be more suitable by actuating a portion of the generated DRR. Based on the user actuation, a new DRR is generated, again from the previously acquired image data, and presented to the user for verification. If the initial match is rejected, for example, the user is able to interactively change the direction and position from where the DRRs are projected until a visual match of the characteristic regions is achieved.

According to another aspect of the invention, increased efficiency and reduced resource consumption may be provided by dynamically selecting the algorithm used to generate the reference DRR from the stored image data. An algorithm from a larger set of multiple algorithms may be (dynamically) selected to generate each DRR. The algorithm is selected to reduce rendering times by selecting the algorithm with the most favorable memory access pattern to produce a new DRR based on the user input received. By allowing variability among the particular techniques used to generate each new DRR, optimal memory access request patterns may be leveraged to reduce rendering time and to provide efficient generation of DRRs.

According to yet another aspect of the invention, processing and memory requirements may be further reduced by generating adaptive multi-resolution DRRs for comparison, rather than full resolution DRRs. In an embodiment, a DRR is first rendered at a lower resolution. Structure detection techniques are then applied to the lower resolution DRR to identify structures within the image. Once identified, the portions of the DRR surrounding the identified edges (e.g., with a threshold pixel distance, for example) are then re-rendered at a higher resolution and then incorporated into the low-resolution DRR resulting in a multi-resolution image. In still further embodiments, the respective sizes of the edge-adjacent portions may be adaptively resized as necessary for more detail, or even further reduced resource consumption. Processing and memory consumption is thereby reduced due to the overall lowered resolution without impacting the effectiveness of the rendered image for manual matching.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Figure 1:
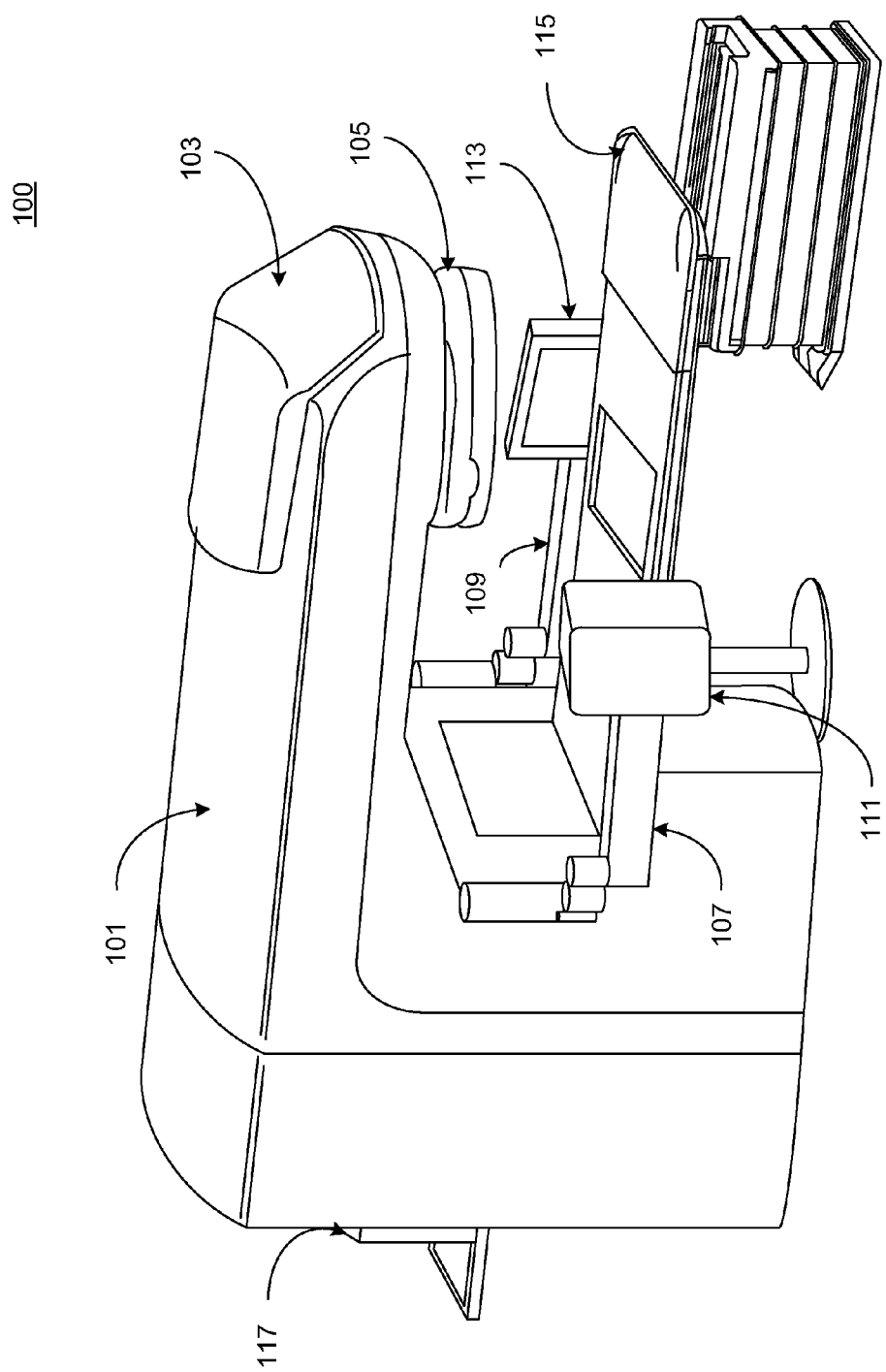
FIG. 1 depicts an illustration of an exemplary radiation therapy and imaging device, in accordance with embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Portions of the detailed description that follows are presented and discussed in terms of a method. Although steps and sequencing thereof are disclosed in figures herein (e.g., FIGS. 3, 4) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-usable medium, such as program modules, executed by one or more computers or other computing devices. Generally, program modules include routines, programs, objects, components, data structures, etc., that perform particular tasks or implement particular abstract data types. The functionality of the program modules may be combined or distributed as desired in various embodiments.

By way of example, and not limitation, computer-usable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information.

Communication media can embody computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above should also be included within the scope of computer-readable media.

Exemplary Radiation Treatment and Imaging Machine

With reference now to FIG. 1, an illustration of an exemplary radiation therapy and imaging device 100 is depicted, in accordance with one embodiment. In one configuration, radiation therapy and imaging device 100 includes a support structure (e.g., gantry 101), a therapeutic radiation source 103 (e.g., a medical linear accelerator) including a treatment head 105, a plurality of robotic arms (e.g., robotic arms 107, 109), a diagnostic radiation source 111, a diagnostic radiation imager 113, and a patient couch 115. In some embodiments, patient couch 115 may have a configurable plurality of degrees of motion (e.g., 4 or 6). In still further embodiments, radiation therapy device 100 may include a communicatively coupled computing device 117 for calculating dosages and processing images.

In one embodiment, the end of gantry 101 positioned above patient couch 115 is attached to a therapeutic radiation source 103. While receiving treatment, a patient is positioned (typically supine) on patient couch 115. Prior to, or during treatment, imaging of a target volume (generally disposed within or about the patient subject) may be performed. According to one embodiment, verification images of the target volume may be acquired by generating a verification image of the area within the patient.

A volumetric image of the area is acquired by, for example, taking a plurality of two-dimensional x-ray cross-sections (also known as scans or slices). The two-dimensional cross-sections x-ray scans may be obtained by rotating the diagnostic radiation source 111 in conjunction with diagnostic radiation imager 113 on around the target volume. The data obtained in the two-dimensional x-ray scans may be subsequently combined according to various algorithms to generate a three dimensional model of the target volume. The data generated from the diagnostic radiation process may be subsequently utilized to provide targeting information which can be used to accurately direct the therapeutic radiation from therapeutic radiation source 103 to the target volume from various angles, such as according to a pre-determined treatment plan.

Exemplary Manual Matching System

Figure 2:
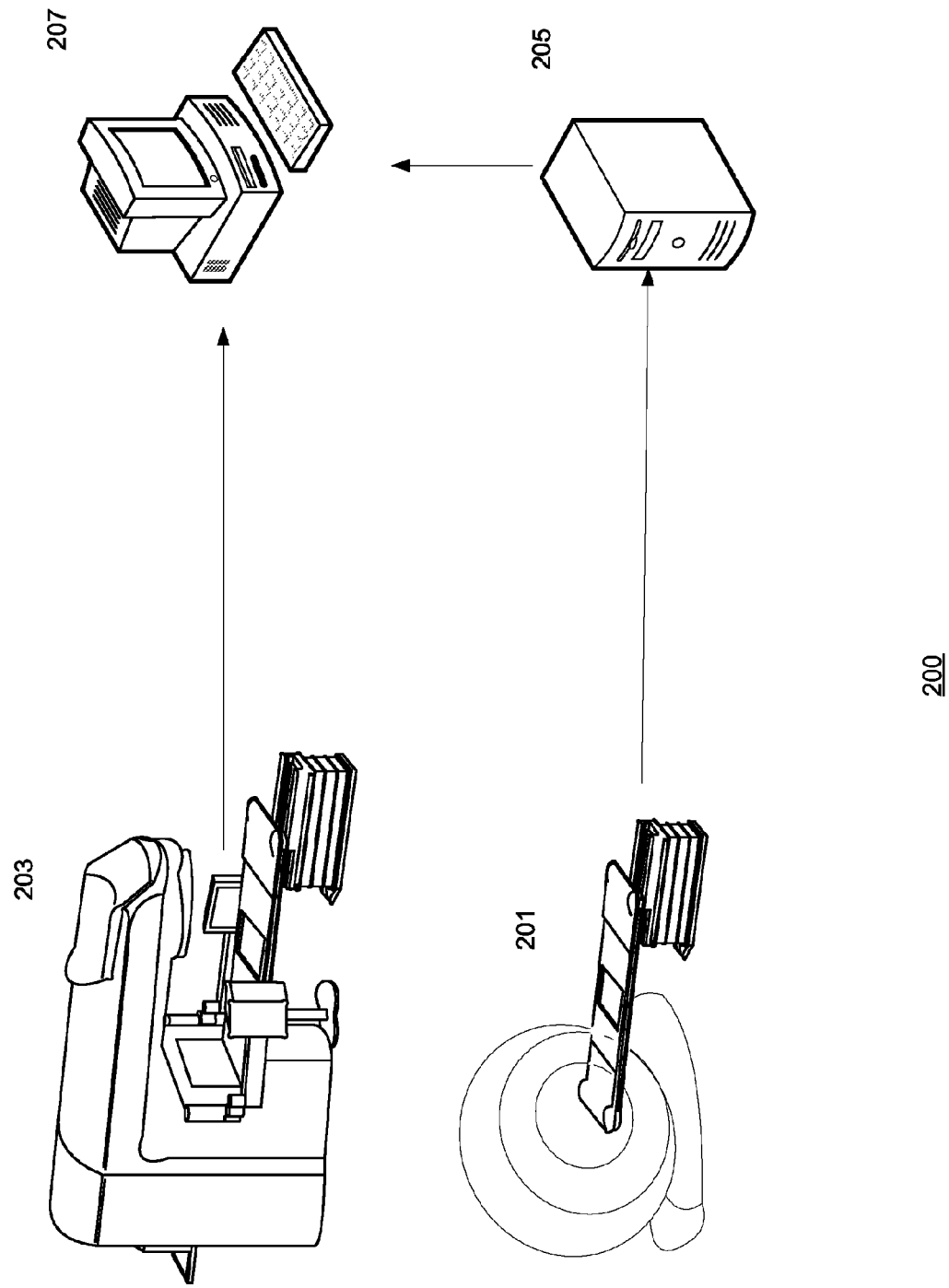
FIG. 2 depicts an illustration of an exemplary system for performing manual matching of generated digitally reconstructed radiographs with verification images, in accordance with embodiments of the present invention.

With reference now to FIG. 2, an illustration of an exemplary system 200 for performing manual matching of generated digitally reconstructed radiographs with verification images is depicted, in accordance with one embodiment. In an embodiment, the system 200 may be implemented as a PACS (Picture Archiving and Communication System), and include a first imaging device 201, a second imaging device 203, a storage device 205, and a workstation 207. The first imaging device 201 may be used to acquire planning images, and may be implemented as diagnostic computer tomography (CT) scanning devices, computer-assisted tomography (CAT) devices, or magnetic resonance imaging (MRI) devices. The second imaging device 203 may comprise a radiation therapy and imaging device as described above with respect to FIG. 1. Storage device 203 may be implemented as a database in a computing system, such as a server, and may be remotely positioned relative to the imaging device 201 and/or the workstation 205. According to an embodiment, imaging data generated by the first imaging device 201 and/or the second imaging device 203 may be expressed according to the DICOM (Digital Imaging and Communications in Medicine) standard.

As depicted in FIG. 2, the first imaging device 201 may be configured to generate planning imaging data for a subject. This imaging data may be stored in storage device 203 via a network connection coupling the storage device 205 and the first imaging device 201, for example. According to an embodiment, the imaging data may correspond to pre-treatment data, and may be generated during the treatment planning stage for the imaging subject. At a subsequent date, during or immediately prior to treatment application, for example, the previously acquired imaging data may be referenced in the storage device 205 and loaded into the workstation 205, also through a network connection or the like. Alternately, data may be loaded into the workstation 205 through computer readable medium, such as through non-rewritable mediums such as compact discs (CD), digital video discs (DVD) and the like, or through rewritable memory devices including volatile and non-volatile memory devices (e.g., external hard drives, flash drives, etc.). At the workstation 207, a user, such as a radiologist, or technician, may be able to verify that the current position of the subject and/or the configuration of the imaging device—communicated to the workstation 207 from the second imaging device 203—corresponds precisely with the position and configuration recorded in the pre-stored data obtained during the treatment planning stage. To perform this verification, images acquired at the second imaging device 201 immediately prior to the application of therapeutic radiation are compared to images acquired with the first imaging device during the planning stage. According to various embodiments, this verification may be performed automatically and/or manually through a user interface displayed by the workstation 207.

Efficient Generation of DRRs

Figure 3:
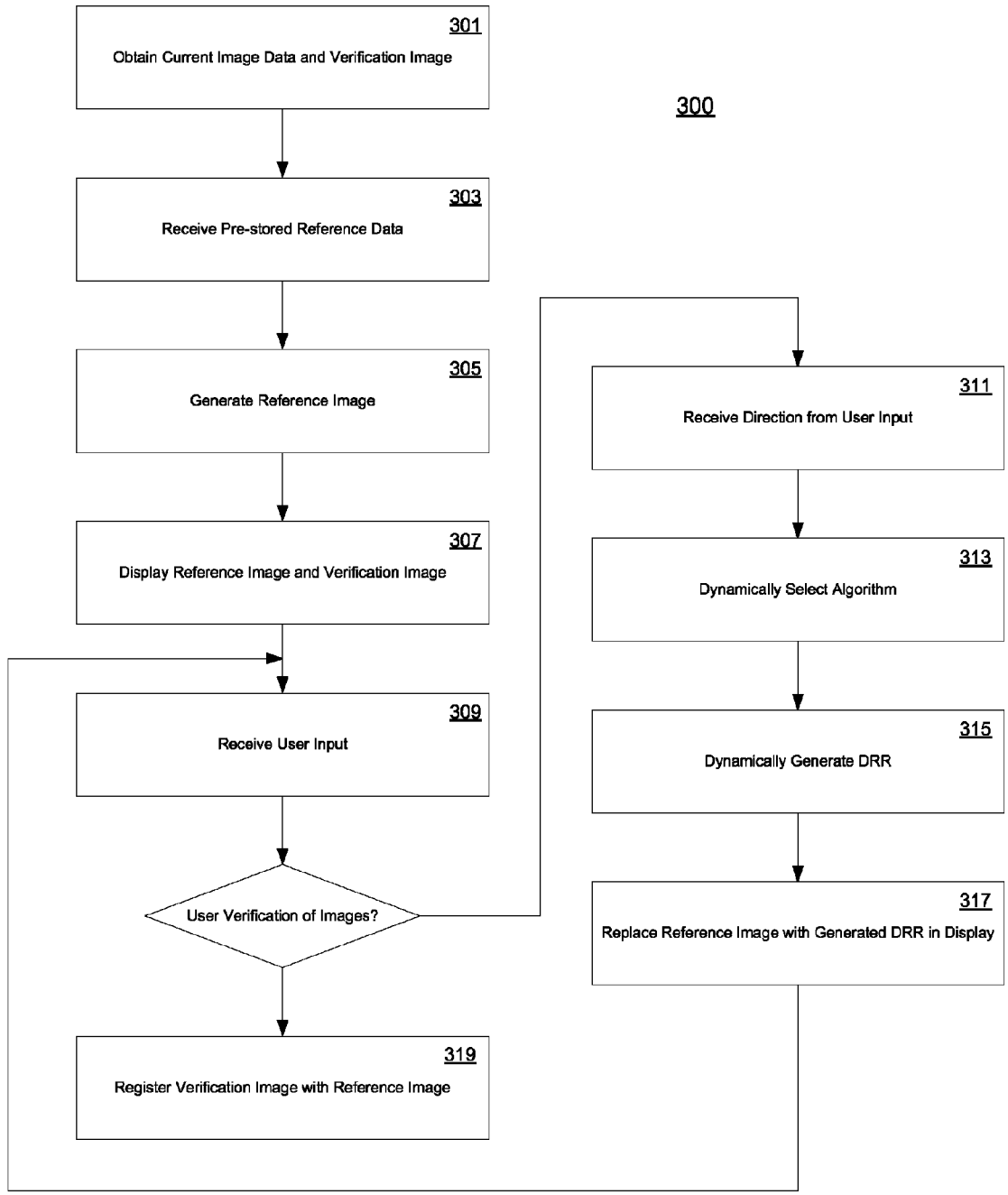
FIG. 3 depicts a flowchart of a method for efficiently generating digitally reconstructed radiographs for manual matching, in accordance with embodiments of the present invention.

With reference now to FIG. 3, a flowchart 300 of a method for efficiently generating digitally reconstructed radiographs for manual matching is depicted, in accordance with one embodiment. Specifically, the method enables the efficient calculation and graphical rendering of DRRs from stored image data by using dynamic selection of image rendering techniques and adaptively rendering DRRs with variably resolutions without impacting the effectiveness of the generated DRRs for manual matching.

In one embodiment, these generated DRRs are used as reference images used in comparison with verification images to confirm a match of the position, displacement, orientation, and other physical characteristics of a target subject with respect to a radiation source, during radiation therapy, for example. Steps 301-317 describe exemplary steps comprising the process depicted in flowchart 300 in accordance with the various embodiments herein described. In one embodiment, the flowchart 300 is implemented as computer-executable instructions stored in a computer-readable medium and executed by a processor in a computing device.

At step 301, image data is acquired. In one embodiment, the real time image data may be acquired from a medical imaging and/or radiation therapy device, such as radiation therapy device 201 described above. The real time image data may include for example, contextual information pertaining to the subject of the imaging/therapy, the position and/or orientation of the subject with respect to the radiation source, the trajectory of the beam produced by the radiation source, the number of target regions with the subject area for which treatment is applied, etc. According to an embodiment, the image data may be used to generate a verification image displaying a target area within the subject.

At step 303, pre-stored reference data is received. The pre-stored reference data may be obtained by referencing a communicatively coupled data storage device (e.g., database 203 in FIG. 2) for pre-stored reference data corresponding to the real time image data received. For example, reference data associated with a subject matching the subject of the image data acquired at step 301 may be accessed. Reference data may further include one or more treatment plans associated with the subject. In an embodiment, the pre-stored reference data is loaded into a workstation (such as workstation 205 of FIG. 2) or other computing device being used to perform manual matching. The pre-stored reference data may, for example, be loaded into a local memory (e.g., RAM) of the workstation.

According to some embodiments, the pre-stored reference data may include previously acquired image data of the subject and/or target area within the subject. According to still further embodiments, the pre-stored reference data includes a three-dimensional image or model of the target area computed by combining a plurality of X-ray slices.

At step 305, an initial reference image is generated from the pre-stored reference data received at step 303. According to some embodiments, the initial reference image may be generated as a computed projection of a three-dimensional model of the target area. The initial reference image may be generated with the same beam and couch characteristics used by the imaging device in acquiring the real time image data. Generation of the initial reference images may be performed according to a dynamically selected algorithm optimized based on the memory layout in the host workstation (see below with respect to step 313).

At step 307, the verification image(s) acquired from image data is displayed to the user of the workstation alongside the corresponding reference image(s). According to embodiments, the verification images and references images are both displayed in a graphical user interface generated in the workstation and displayed in a display device (such as a monitor, or screen) communicatively coupled to the workstation. According to some embodiments, each reference image may be displayed adjacent or otherwise proximate to its respective corresponding verification image. In still further embodiments, a verification image may be displayed at a first scale and/or in a display at a first size immediately adjacent to its corresponding reference image having the same size and scale for added convenience and ease during comparison. A second display of the same verification image may be displayed at a nonequivalent scale and/or size apart from the above paired displays, for increased viewing detail, for example. In some embodiments, the second display may instead comprise an overlay of the verification image over the reference image, at the same scale.

According to various embodiments, user input may be solicited via user input controls that allow the user (e.g., technician, radiologist, etc.) submit user input in order to verify or reject a match between the displayed verification and reference images. User input, received at step 309, may be submitted via a user input device, such as a mouse, keyboard, control pad, etc. Alternately, according to some implementations, the display device may be implemented as a touch screen. According to these implementations, user input may be received using a stylus, the user's finger, etc. directly on the display screen. In an embodiment, user input controls may be implemented as on-screen graphical buttons labeled as either "ACCEPT" or "ACCEPT MATCH" (or some derivation thereof), which when actuated, register the appropriate action. Progression through the process depicted in flowchart 300 is dependent on the user input submitted in response to the displayed images at step 307.

For example, user actuation of the graphical button labeled "ACCEPT" would cause the process to proceed directly to step 319, and generate a system registration of the verification image with the produced reference image. This registration may be saved, in a table, for example, and added or updated to the reference data stored in the data storage device. Once registration is ended, another match may be confirmed from subsequently displayed verification images, whereupon the process depicted in flowchart 300 may be repeated. Alternately, manual matching may be terminated upon the successful registration of the display verification image with a previously acquired reference image via user actuation on the "CANCEL" button.

Alternately, a user may reject the display reference image by actuated directly on the image. In an embodiment, the user is able to reject the displayed reference image in lieu of another reference image generated along another direction, with respect to the target subject. For example, a user may determine, based on the displays of the verification image and the previously generated reference image, that the reference image is incongruent along the horizontal and/or vertical axis with respect to the verification image. Accordingly, the user is able to request a generation of another reference image in a more preferable direction by actuating in a direction within the displayed reference image. According to an embodiment, user input may be received at step 311 which corresponds to an orthogonal direction with respect to the display reference image, and generation of a subsequent reference image may be performed in the indicated direction.

Generation of a new reference image in a given direction may be performed using one or more techniques. At step 313, a technique (e.g., an algorithm) may be dynamically determined for the direction indicated by the input received at step 311 from a set of available techniques. Each technique generates a projection of the target volume from a three dimensional model of the target volume. Further, each technique may generate the projection using an inherent (and unique) memory access pattern. According to some embodiments, the technique dynamically selected at step 313 is the technique with the optimal memory access pattern that corresponds to the layout in the local memory of the three dimensional image upon which the new generated reference image is based—for the indicated direction. According to further embodiments, while a reference image may be generated in any direction according to any of the available techniques, each of the available (orthogonal) directions will correspond to a technique with a memory access pattern superior to that of all other available techniques.

The superior or optimal memory access pattern may be determined by, for example, comparing the addresses in the local memory of the three dimensional image with the target address of the memory access pattern for each technique and selecting the technique with the access pattern most proximate to the addresses in memory of the three dimensional image. For example, given the projection direction, each technique of the set of techniques will result in a specific memory access pattern. The technique generating the most sequential memory access pattern for the given projection direction will be chosen. Other layout specific characteristics, including specific memory hierarchies (e.g., processor cache, volatile memory, non-volatile memory) may also be factored into the determination of the technique selected. The set of techniques for generating the reference image may include at least a ray-casting technique and a slicing technique, for example.

At step 315, the new reference image is generated in the direction indicated at step 311 and using the technique dynamically determined at step 313. The new reference image may be generated as an adaptive, multi-resolution DRR according to some embodiments (see below with respect to FIG. 4). Finally, the previously generated reference image displayed at step 307 in the graphical user interface is replaced with a display of the reference image dynamically generated at step 315. Steps 309 through 317 may be thereafter repeated until the generated reference image is manually confirmed by the user to be a successful match with the acquired verification image.

Generation of Adaptive, Multi-Resolution DRR

Figure 4:
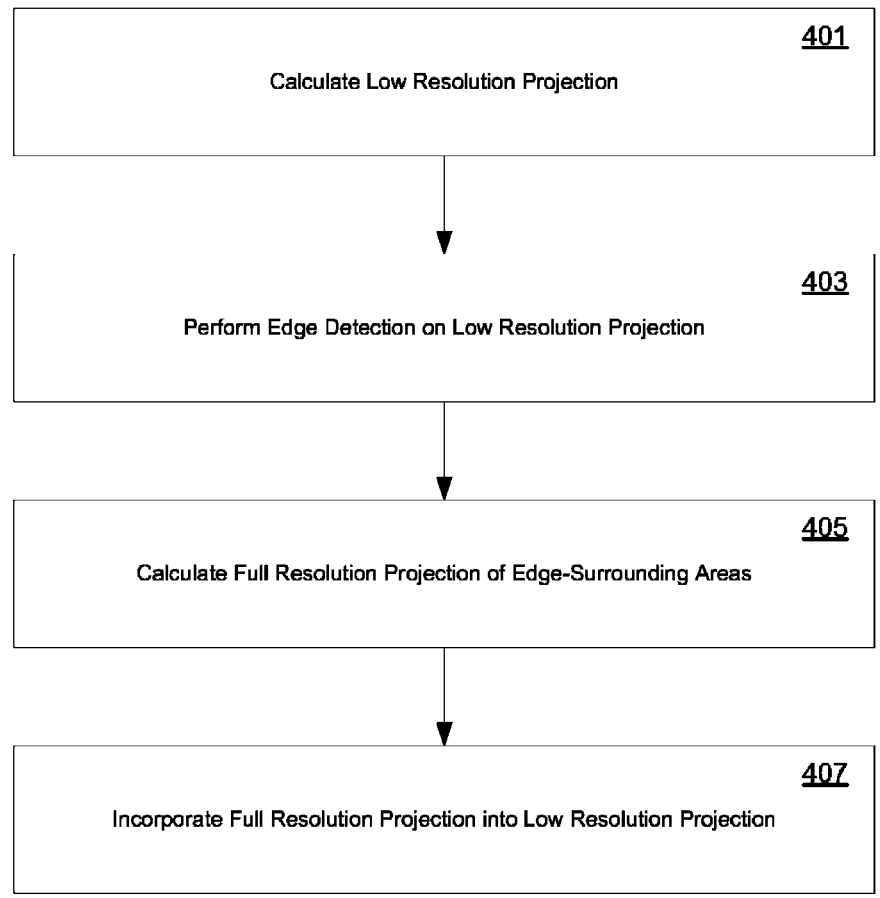
FIG. 4 depicts a flowchart of a method for efficiently generating adaptive, multi-resolution digitally reconstructed radiographs for manual matching, in accordance with embodiments of the present invention.

FIG. 4 depicts a flowchart 400 of a method for efficiently generating adaptive, multi-resolution digitally reconstructed radiographs for manual matching, in accordance with one embodiment. The adaptive, multi-resolution DRR may be generated in response to determining a user actuation on a previously rendered display of a reference image; alternately, an adaptive, multi-resolution DRR may be generated as an initial reference image with beam and/or device characteristics that match the characteristics of a verification image. Steps 401-415 describe exemplary steps comprising the process depicted in flowchart 400 in accordance with the various embodiments herein described. In one embodiment, the flowchart 400 is implemented as computer-executable instructions stored in a computer-readable medium and executed with an imaging and/or image matching application on a host computing device or workstation. According to a further embodiment, this technique may be performed during a process of generating a DRR for display in a graphical user interface, such as during step 313 of the process 300 described above with respect to FIG. 3.

At step 401, a low resolution projection of an imaging subject or a target volume of the imaging subject is calculated from pre-stored reference data. The low resolution projection may be calculated using a technique (dynamically) selected in step 311 of the process 300 described above. Producing a low resolution projection may be performed by generating the projection with relatively few pixels corresponding to a default setting (as determined by the image and/or matching application) or a threshold, and may comprise a display resolution with less pixels overall and less pixels per square inch of display, for example.

At step 403, an edge detection technique is performed on the low resolution projection to determine edges and to delineate structures within the projection. Structures may comprise, for example, bones, organs, soft tissue components or portions thereof. Edge detection may be performed according to various well-known techniques. Once the edges in the projection are determined, regions proximate to the detected edges are re-rendered in full resolution at step 405. The regions proximate to the detected edges may include, for example, the areas of the projection within a threshold distance, or within a number of pixels. Any portions of the projection falling within that threshold may be re-rendered in higher resolution than the resolution calculated at step 401. According to an embodiment, the portions of the projections determined to be proximate to the detected edges may be rendered at the maximum (full) resolution allowable to the image and/or image matching application.

Finally, at step 407, the portions of the projection rendered in high (or max) resolution are incorporated into the low resolution projection to create a multi-resolution projection. According to still further embodiments, the exact resolution of the higher resolution portions may be adapted based on the projection itself. For example, for a projection containing several structures or organs, and therefore, likely to contain several edges, the areas surrounding the edges may be re-rendered in a higher resolution than the original low resolution projection calculated at step 401, but lower than the maximum resolution possible, to reduce processing times and memory requirements. Alternately, the distance from the determined edge to render at the higher resolution may also be adjusted based on the amount of high-resolution subject matter determined in the projection. According to such implementations, for example, in a projection containing a high number of detected edges, the distance from each edge that is rendered at a higher resolution may be adaptively reduced. In still further embodiments, the image may be rendered in a number of resolutions, such that the resolution of portions in the image are rendered inversely proportional to the distance from detected edges. Thus for example, areas of an image within a first threshold distance from detected edges may be rendered at high resolution, images between a first and second (larger) threshold distance from detected edges are rendered at a medium image, and distances beyond the second threshold distance from the detected edges are rendered at the lowest resolution.

Exemplary Computing Device

Figure 5:
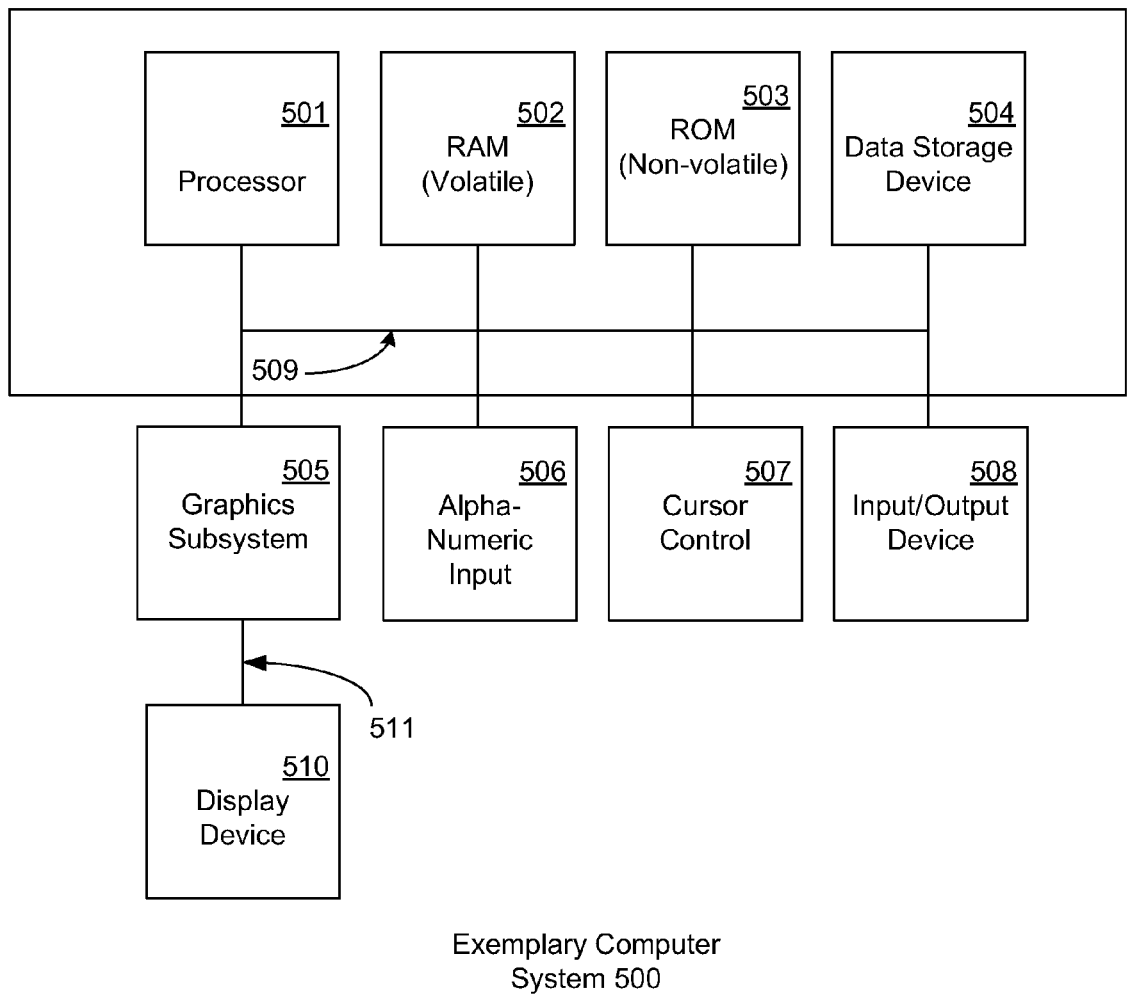
FIG. 5 depicts an exemplary computing environment upon which embodiments of the present invention may be implemented.

As presented in FIG. 5, an exemplary system upon which embodiments of the present invention may be implemented includes a general purpose computing system environment, such as computing system 500. In its most basic configuration, computing system 500 typically includes at least one processing unit 501 and memory, and an address/data bus 509 (or other interface) for communicating information. Depending on the exact configuration and type of computing system environment, memory may be volatile (such as RAM 502), non-volatile (such as ROM 503, flash memory, etc.) or some combination of the two.

Computer system 500 may also comprise an optional graphics subsystem 505 for presenting information to the computer user, e.g., by displaying information on an attached display device 510, connected by a video cable 511. According to embodiments of the present claimed invention, the graphics subsystem 505 may be coupled directly to the display device 510 through the video cable 511. A graphical user interface of an application for controlling a medical linear accelerator executing in the computer system 500 may be generated in the graphics subsystem 505, for example, and displayed to the user in the display device 510. In alternate embodiments, display device 510 may be integrated into the computing system (e.g., a laptop or netbook display panel) and will not require a video cable 511. In one embodiment, the processes 300, 500, 600, 700, and 800 may be performed, in whole or in part, by graphics subsystem 505 in conjunction with the processor 501 and memory 502, with any resulting output displayed in attached display device 510.

Additionally, computing system 500 may also have additional features/functionality. For example, computing system 500 may also include additional storage (removable and/or non-removable) including, but not limited to, magnetic or optical disks or tape. Such additional storage is illustrated in FIG. 5 by data storage device 507. Computer storage media includes volatile and nonvolatile, removable and non-removable media implemented in any method or technology for storage of information such as computer readable instructions, data structures, program modules or other data. RAM 502, ROM 503, and data storage device 507 are all examples of computer storage media.

Computer system 500 also comprises an optional alphanumeric input device 506, an optional cursor control or directing device 507, and one or more signal communication interfaces (input/output devices, e.g., a network interface card) 509. Optional alphanumeric input device 506 can communicate information and command selections to central processor 501. Optional cursor control or directing device 507 is coupled to bus 509 for communicating user input information and command selections to central processor 501. Signal communication interface (input/output device) 509, also coupled to bus 509, can be a serial port. Communication interface 509 may also include wireless communication mechanisms. Using communication interface 509, computer system 500 can be communicatively coupled to other computer systems over a communication network such as the Internet or an intranet (e.g., a local area network), or can receive data (e.g., a digital television signal).

Exemplary Graphical User Interface

Figure 6:
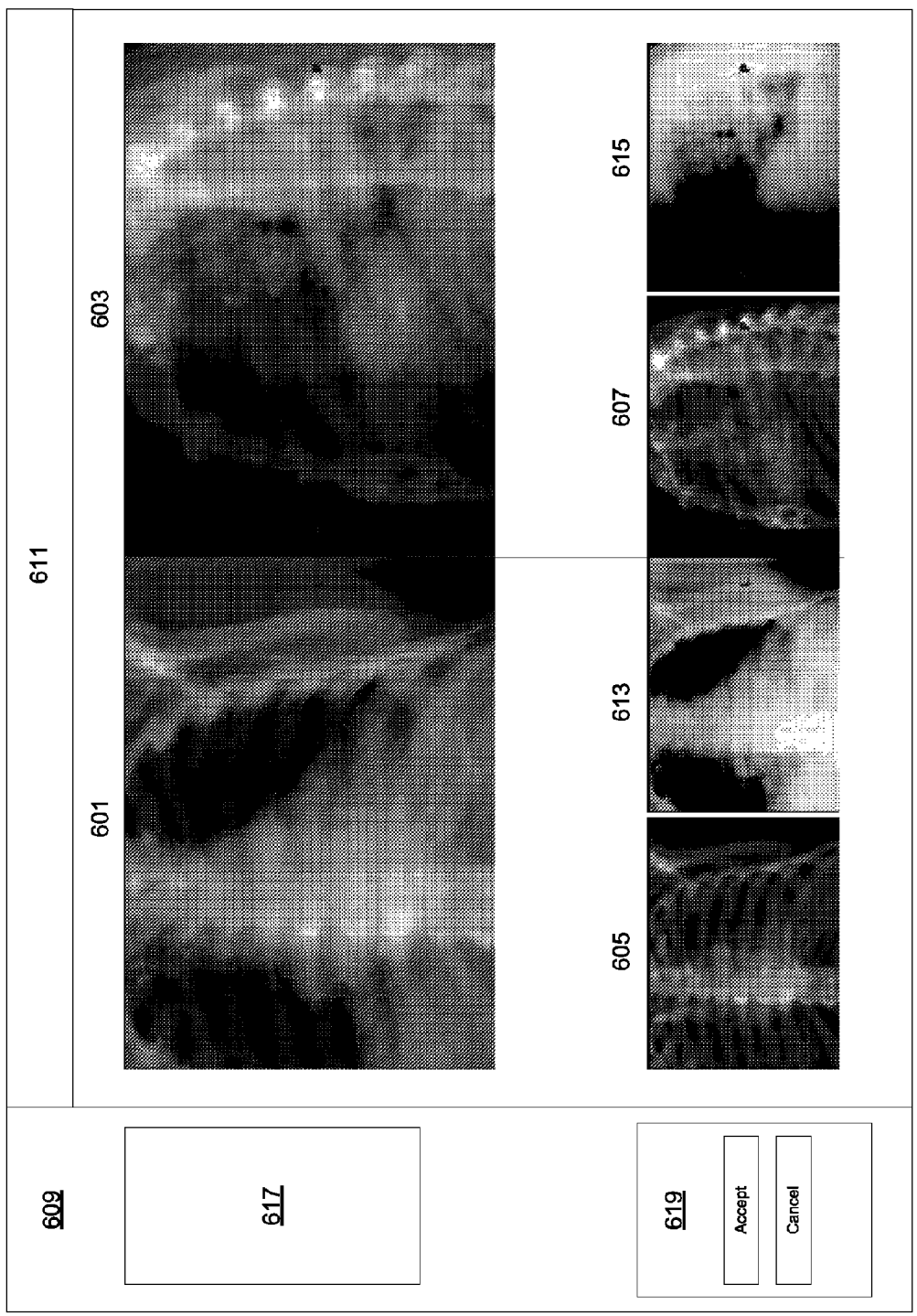
FIG. 6 depicts an exemplary on-screen graphical user interface produced in a system for performing manual matching of generated digitally reconstructed radiographs with verification images, in accordance with embodiments of the present invention.

FIG. 6 depicts an exemplary on-screen graphical user interface 600 produced in a system for performing manual matching of generated digitally reconstructed radiographs with verification images, in accordance with an embodiment. In an embodiment, the graphical user interface 600 may be generated from an image matching application executed on a computing device or workstation (e.g., workstation 205) communicatively coupled to an imaging device (e.g., imaging device 201) and/or to a database of pre-stored data (e.g., database 203). In a further embodiment, a subset of the pre-stored data in the database corresponding to the image subject of the imaging device may be loaded on the workstation 205 during a matching session, such that references to the database are minimized. As depicted in FIG. 6, user interface 600 displays a pair of verification image displays (e.g., first verification image display 613, second verification image display 615) configured to display current image data, with a corresponding pair of reference image displays (e.g., first reference image display 605, second reference image display 607) generated from pre-stored reference data and a pair of overlay image displays (e.g. overlay display 601, overlaying first verification image with first reference image, and overlay display 603, overlaying second verification image with second reference image). Configuration Panel 609, and File and ID panel 611 complete the user interface depicted in the user interface 600 of FIG. 6.

As discussed herein, verification images may correspond to image data being obtained in real time by a communicatively coupled imaging device (e.g., imaging device 201 described above). According to an embodiment, overlay image displays (601, 603) may be of a larger scale than reference and verification image displays (605, 607, 613, 615). According to these embodiments, a second, larger display may be generated and displayed that presents the overlay of each verification image over the corresponding reference image (e.g., first overlay image display 601 corresponds to first verification image display 613 and first reference image display 605, and second overlay verification image display 603 corresponds to second verification image display 615 and second reference image display 607). As depicted in FIG. 6, the verification displays (613, 615) may be generated according to the same scale as the reference image displays (605, 607), and may appear in the user interface immediately adjacent to the reference image displays 605, 607. While user interface 600 is depicted in FIG. 6 with a plurality of verification image displays with a like number of reference image displays (in this case, two of each), it is to be understood that alternate embodiments are well suited to display greater or fewer number of images of either type.

According to an embodiment, Configuration Panel 609 may include a patient support (for example, couch) display 617 and a match interface 619. Patient support display 617 may display current position characteristics for the patient support device, target position characteristics for the patient support device (based on corresponding data from reference image data), and the delta or shift between current and target positions, for example. These characteristics may include, for example, spatial characteristics corresponding to the position of the subject; and/or characteristics of the platform upon which the image subject is resting (e.g., a couch). Platform characteristics may include, for example, the height, lateral position, displacement, pitch, roll, axes, etc. of the platform. Match interface 619 may display functionality (e.g., via a graphical button) that, when actuated with a user input device, allows a user of the user interface 600 to confirm ("accept") or reject a match between a displayed verification image and a generated projection displayed as a reference image or terminate "cancel" the manual match application. Accepting a match through the match interface 619 may cause the image system to register the verification image with the reference image (and corresponding image data). This registration may include the spatial transformation between the reference image coordinate system and the verification image coordinate system, as well as particular beam, and platform characteristics and a generated specific identification number that associates the particular images. According to further embodiments, this registration, once verified by the user, may also be manually or automatically stored within the database of the system. In still further embodiments, Match interface 619 may display further functionality to alternate reference images (e.g., generate projections) from the pre-stored reference data.

File and ID panel 611 may display functionality that allows a user to load and/or select a particular imaging device to receive image data from, and to load and/or select a file or directory in the database to receive pre-stored reference data. File and ID panel 611 may also display identification information of the imaging subject, as well as further controls to designate and load the subject matter displayed in user interface 600.

As described herein, users of the system may perform manual matching of verification images obtained in real time with reference images dynamically generated from pre-stored reference data. According to an embodiment, pre-stored reference data contained in the database (e.g., database 205) may be automatically accessed and searched for image data corresponding to the image subject, such as the treatment plan of the image subject, and/or having characteristics (such as beam characteristics or platform characteristics) matching that of the verification image. An image determined to include at least these characteristics may be selected to be displayed as an initial reference image in the reference image display (605, 607). If, however, the user is unsatisfied with the generated initial reference image, or prefers to compare additional images, the user may elect to view additional images generated from projections of the reference data. Using a user input device (e.g., a mouse, stylus, track pad, keyboard, etc.), a user is able to indicate—via an actuation of the user input device—a direction within the reference image display (605, 607). According to some embodiments, the direction may be any one of set of orthogonal directions from the center of the display, and/or substantially lying on or near the border.

Once a direction from user input is detected, a digitally reconstructed radiograph (DRR) is dynamically generated in the host computing device or workstation from the loaded reference data. According to an embodiment, the DRR is generated to correspond to a projection of a computer-constructed three dimensional volume of the image subject or a target volume within the image subject. User input corresponding to a particular direction of the reference image in the reference image display (605, 607) would generate a reference image from the three-dimensional volume with a shift in the direction indicated by the user input from the previously displayed reference image. That is, if the user actuates on a left portion of the reference image display (605, 607), a DRR will be dynamically generated that displays the target volume of the image subject with a corresponding shift to the left. In further embodiments, the degree of the shift will be synchronized to conform with the movement of the user actuation.

As described herein, the DRR may be generated according to a plurality of techniques including (but not limited to) slicing and ray-casting. According to various embodiments, the particular selection of the technique used to generate the particular DRR depends on the memory access pattern of each technique and the memory layout of the volume image used to generate the DRR in the host computing device or workstation. The technique with the memory access pattern closest to the memory layout of the volume image is dynamically determined, and used to generate the DRR, thereby optimizing the read time required to generate the DRR without requiring undue overhead in memory as would be required for conventional DRR generation methods.

Adaptive Multi-Resolution DRR

Embodiments of the present invention are described herein to dynamically generate digitally reconstructed radiographs from pre-stored image data in an efficient manner that requires neither potentially lengthy pre-computation nor additional storage. To avoid requiring pre-computation or additional storage, the DRRs may be generated with adaptive, multiple resolutions. An adaptive, multi-resolution DRR may be generated by, for example, rendering an image in low resolution; performing edge detection to define structures within the image; and rendering portions of the image corresponding to areas around the detected edges in full resolution. According to an embodiment, pixels in the image within a certain threshold of distance of a detected edge may be re-rendered under full resolution, with all other pixels in the image unchanged. By using such an implementation, structural identification is emphasized by whereas processing required to render non structural areas may be avoided to minimize processing and space requirements.

Figure 7A:
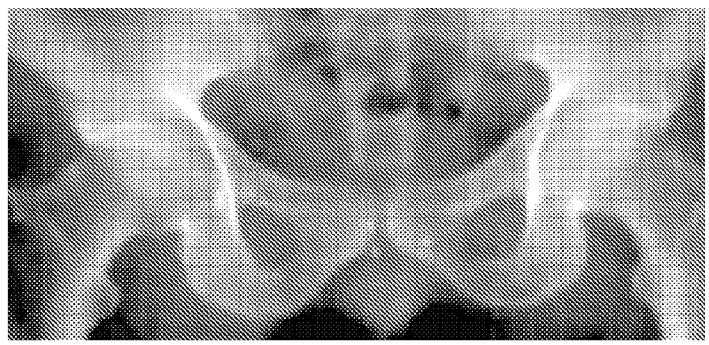
FIG. 7a depicts an exemplary on-screen display of an adaptive, multi-resolution digitally reconstructed radiograph produced in accordance with embodiments of the present invention.
Figure 7B:
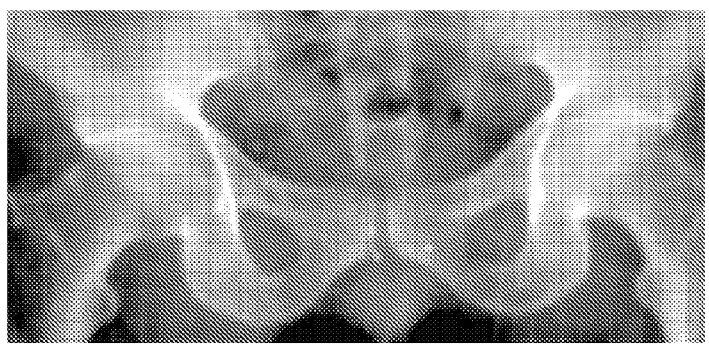
FIG. 7b depicts an exemplary on-screen display of a full resolution digitally reconstructed radiograph produced in accordance with embodiments of the present invention.
Figure 7C:
FIG. 7c depicts an exemplary on-screen display of an adaptive, multi-resolution digitally reconstructed radiograph with indicated portions that are produced with full resolution, generated in accordance with embodiments of the present invention.

FIGS. 7*a*-7*c* depict exemplary images of the same region produced according to these features. FIG. 7*a* depicts an exemplary on-screen display 700*a* of an adaptive, multi-resolution digitally reconstructed radiograph produced in accordance with embodiments of the present invention. As depicted in FIG. 7*a*, the edges defining visible structures and the areas surrounding the edges are rendered with a higher graphical resolution than non-edge adjacent areas. FIG. 7*b* depicts an exemplary on-screen display 700*b* of a full resolution digitally reconstructed radiograph produced in accordance with embodiments of the present invention. As depicted in FIG. 7*b*, all pixels within the image are rendered with full resolution, which would necessitate longer processing and greater storage requirements. According to various embodiments of the subject invention, the visual quality of the image depicted in FIG. 7*a* approximate the visual quality of the image depicted in FIG. 7*b*, but would require substantially less computation time. FIG. 7*c* depicts an exemplary on-screen display of a digitally reconstructed radiograph 700*c* with indicated portions that are produced with full resolution, generated in accordance with embodiments of the present invention.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for performing image mapping for computer tomography, the method comprising:
   generating a reference image based on a pre-stored reference data and a verification image corresponding to an imaging subject;
   displaying the reference image proximate to the verification image in an on-screen graphical display;
   receiving, a user input corresponding to a position within the on-screen graphical display, the user input being indicative of a direction within the reference image;
   in response to receiving the user input indicative of the direction, dynamically selecting an algorithm from a plurality of digitally reconstructed radiograph (DRR) generating algorithms based on the direction indicated by the user input;
   generating a DRR corresponding to the direction indicated by the user input from the pre-stored reference data with the dynamically selected algorithm, the DRR having a first resolution;
   identifying a plurality of structures in the DRR and a plurality of edges surrounding the plurality of structures;
   rendering a portion of the DRR within a threshold distance of the plurality of edges surrounding the identified plurality of structures in a second resolution being a different resolution than the first resolution; and
   incorporating the portion with the second resolution into the DRR.

2. The method according to claim 1, further comprising, in response to receiving the user input indicative of the verification of the visual match between the generated DRR and the verification image, replacing a registration associating the reference image and the verification image with a registration associating the generated DRR with the verification image.

3. The method according to claim 1, wherein the reference image is generated from pre-stored reference data comprising a three dimensional image of the imaging subject.

4. The method according to claim 3, wherein the reference image is generated from a current image data of the imaging subject, the current image data comprising imaging subject information and image acquisition information.

5. The method according to claim 4, wherein the image acquisition information comprises a plurality of imaging beam characteristics.

6. The method according to claim 5, further comprising generating a reference image comprising a first projection based on the pre-stored reference data and a verification image of the imaging subject.

7. The method according to claim 4, wherein the current image data further comprises configuration information corresponding to a plurality of treatment device configurations of a radiation therapy device communicatively coupled to the imaging device.

8. The method according to claim 7, wherein the dynamically generating a DRR from the pre-stored reference data with the selected algorithm comprises generating a second projection of the imaging subject from the three dimensional image, the second projection having a configuration information matching the configuration information of the current image data from the pre-stored reference data.

9. The method according to claim 7, wherein the dynamically generating a DRR from the pre-stored reference data with the selected algorithm comprises generating the adaptive multi-resolution projection of the imaging subject.

10. The method according to claim 3, wherein the pre-stored reference data is stored in a database in a computing system communicatively coupled to the database and executing an image matching module.

11. The method according to claim 10, wherein the computing system comprises a picture archiving and storage system (PACS) device.

12. The method according to claim 10, wherein the computing system comprises a Digital Imaging and Communications in Medicine (DICOM) server.

13. The method according to claim 10, wherein each algorithm of the plurality of algorithms uses a corresponding memory access pattern to access data stored in a memory device of the computing system.

14. The method according to claim 13, wherein each algorithm of the plurality of algorithms has a memory access pattern that is distinct from a memory access pattern corresponding to every other algorithm of the plurality of algorithms.

15. The method according to claim 14, wherein the direction corresponds to a three-dimensional image, and wherein dynamically selecting an algorithm comprises dynamically selecting the algorithm with the most sequential memory access pattern corresponding to the direction indicated by the user input.

16. The method according to claim 1, wherein the direction within the reference image corresponds to a movement of a user input device within the on-screen graphical display of the reference image.

17. The system according to claim 16, wherein the algorithm dynamically selected from the plurality of DRR generating algorithms comprises the algorithm with a corresponding a memory access pattern that most closely approximates a layout in the memory that stores a portion of the pre-stored reference data corresponding to the first direction indicated by the user input.

18. The method according to claim 1, wherein an algorithm of the plurality of DRR generating algorithms comprises manipulating the volumetric 3D image data with a ray casting technique.

19. The method according to claim 1, wherein an algorithm of the plurality of DRR generating algorithms comprises manipulating the volumetric 3D image data with a slicing technique.

20. A system for performing image mapping in computer tomography, the system comprising:

an imaging device operable to perform medical imaging of an image subject to generate a verification image, the medical imaging being performed on the image subject according to a plurality of acquisition characteristics and a plurality of subject context characteristics;

a database operable to store a pre-stored reference data of the image subject;

a computing system operable to execute an image matching module, the computing system comprising;

a memory, operable to receive the pre-stored reference data from the database;

a processor, communicatively coupled to the memory and operable to dynamically generate a digitally reconstructed radiograph (DRR) from the pre-stored reference data using an algorithm dynamically selected from a plurality of algorithms, the DRR having a first resolution;

a display device, communicatively coupled to the processor, and operable to display the verification image and the generated DRR; and a user input device, operable to receive user input indicative of a first direction within the generated DRR and to receive user input indicative of a verification of a visual match between the generated DRR and the verification image, wherein the processor selects the algorithm corresponding to the direction indicated by the user input device and generates a new DRR corresponding to the direction indicated based on the selected algorithm, further wherein, a plurality of structures and a plurality of edges surrounding the plurality of structures in the DRR are identified, and a portion of the generated DRR within a threshold distance of the plurality of edges surrounding the plurality of structures is rendered in a second resolution and incorporated into the DRR.

21. The system according to claim 20, wherein the user input device comprises at least one of: a mouse; a stylus; and a keyboard.

22. The system according to claim 21, wherein the processor is further operable to generate a second DRR using an algorithm selected from the plurality of DRR generating algorithms based on a second direction received as a second user input from the user input device.

23. The system according to claim 20, wherein the plurality of DRR generating algorithms comprises a ray casting technique; and a slicing technique.

24. The system according to claim 20, wherein each algorithm of the plurality of DRR generating algorithms uses a distinct corresponding memory access pattern to access the pre-stored reference data stored in the memory.

25. A computer readable medium containing program instructions embodied therein for causing a computing system to generate digitally reconstructed radiographs for manual matching, the program instructions comprising:

instructions to generate a reference image based on a pre-stored reference data and a verification image corresponding to an imaging subject;

instructions to display the reference image proximate to the verification image in an on-screen graphical display;

instructions to receive a user input corresponding to a position within the on-screen graphical display, the user input being indicative of a direction within a display of the reference image;

instructions to dynamically select an algorithm from a plurality of digitally reconstructed radiograph (DRR)

generating algorithms corresponding to the direction indicated by the user input;

instructions to dynamically generate a DRR corresponding to the direction indicated by the user input from the pre-stored reference data with the selected algorithm, the DRR having a first resolution;

instructions to identify a plurality of structures in the DRR;

instructions to render a portion of the DRR within a threshold distance surrounding the identified plurality of structures in a second resolution, the second resolution comprising a different resolution than the first resolution; and instructions to incorporate the portion with the second resolution into the DRR.

26. The computer readable medium according to claim 25, wherein the instructions to dynamically select an algorithm from a plurality of algorithms comprises instructions to select an algorithm with a partial memory access request that most approximates a memory layout of a portion of the pre-stored reference data used to generate the DRR.

* * * * *